(12) United States Patent
Komissarova et al.

(10) Patent No.: US 8,043,859 B2
(45) Date of Patent: Oct. 25, 2011

(54) QUALITY CONTROL MIXTURE FOR GLYCINE TABLETS, A METHOD FOR PREPARING THE MIXTURE AND A METHOD FOR IDENTIFYING THE MIXTURE

(75) Inventors: Irina Alekseevna Komissarova, Moscow (RU); Tatjyana Dmitrievna Soladatenkova, Moscow (RU); Yuliya Vasiljevna Gudkova, Zelenograd (RU); Tatjyana Tikhonovna Kondrashova, Moscow (RU); Nataljya Mikhayjlovna Burbenskaya, Moscow (RU)

(73) Assignee: Nekommercheskoe Uchrezhdenie "Nauchno-Issledovateljskiyj Institut Citokhimii I Molekulyarnoyj Farmakologii", Moscow (RU)

( * ) Notice: Subject to any disclaimer, the term of this patent is extended or adjusted under 35 U.S.C. 154(b) by 0 days.

(21) Appl. No.: 12/821,916

(22) Filed: Jun. 23, 2010

(65) Prior Publication Data
US 2011/0014711 A1    Jan. 20, 2011

Related U.S. Application Data

(63) Continuation of application No. PCT/RU2008/000130, filed on Mar. 6, 2008.

(30) Foreign Application Priority Data
Mar. 7, 2007  (RU) ................................ 200700597

(51) Int. Cl.
G01N 33/68   (2006.01)
G01N 33/00   (2006.01)

(52) U.S. Cl. ............... 436/89; 436/8; 436/17; 436/164; 436/166; 436/174

(58) Field of Classification Search ............... 436/8, 17, 436/86, 89, 164, 166, 174, 175
See application file for complete search history.

(56) References Cited

U.S. PATENT DOCUMENTS

| | | | | |
|---|---|---|---|---|
| 5,534,262 A | * | 7/1996 | Dobrotvorsky et al. | 424/464 |
| 5,643,954 A | * | 7/1997 | Komissarova et al. | 514/561 |
| 5,731,349 A | * | 3/1998 | Komissarova et al. | 514/561 |
| 7,858,377 B2 | * | 12/2010 | Komissarova et al. | 436/89 |
| 2004/0029966 A1 | * | 2/2004 | Komissarova | 514/561 |

FOREIGN PATENT DOCUMENTS

| | | |
|---|---|---|
| EA | 007615 B1 | 12/2006 |
| RU | 2012869 C1 | 5/1994 |
| RU | 2171673 C1 | 8/2001 |
| SU | 1361477 A1 | 12/1987 |

OTHER PUBLICATIONS

International Search Report, mailed Sep. 11, 2008, from PCT/RU2008/000130, filed Mar. 6, 2008.

Gosudarstvennaya Farmakopeya SSSR. Desyatoe izdanie. Meditsina, Moscow, 1968, pp. 667-669.

* cited by examiner

*Primary Examiner* — Maureen Wallenhorst
(74) *Attorney, Agent, or Firm* — Houston Eliseeva, LLP

(57) ABSTRACT

A method is described for preparing a mixture for quality control of 0.1 g glycine tablets for sublingual application. The mixture for quality control includes a 100:0.5 ratio of ethanol to porphyrized tablets, each tablet containing 0.1 g microcapsules of non-agglomerated crystals of amino-acetic acid covered with a polymeric film of water-soluble methylcellulose, each tablet further containing 0.001 g of magnesium stearate. The process for preparing the mixture includes dissolution of the tablet in ethanol for 20 minutes and is carried out at a temperature of 40° C. in an apparatus using a paddle rotation speed of 200 revolutions per minute. After the mixture is dissolved, it is allowed to stand for 10 minutes at room temperature, and then a light transmission coefficient is measured at 700±2 nm for a 10 mm thick layer of the mixture. A transmission value within the limits of 90% to 100% compared with 50% ethanol corresponds to the proper quality.

3 Claims, No Drawings

QUALITY CONTROL MIXTURE FOR GLYCINE TABLETS, A METHOD FOR PREPARING THE MIXTURE AND A METHOD FOR IDENTIFYING THE MIXTURE

RELATED APPLICATIONS

This application is a Continuation of PCT application serial number PCT/RU2008/000130 filed on Mar. 6, 2008 which claims priority to Eurasian application EA 200700597 filed on Mar. 7, 2007, both of which are incorporated herein by reference in their entirety.

BACKGROUND OF THE INVENTION

The invention relates to the chemical-pharmaceutical industry and specifically to mix for identification test in the process of quality control of the medicine "Glycine tablets for sublingual applying 0.1 g", methods of its preparation and identity evaluation during quality control of the specified medicine.

The medicine "Glycine tablets for sublingual applying 0.1 g" (hereinafter referred to as Glycine) activates inhibitory processes in central nervous system, exhibits properties of $\alpha_1$ adrenoceptor blocking agent and has stressprotecive, antistress, nootropic andxieuroprocrive effect.

For production of the medicine "Glycine tablets for sublingual applying 0.1 g" there are used microcapsules in the form of non-agglomerated crystals of amino-acetic acid filmed by water-soluble methyl-cellulose, MC-100 and magnesium stearate. Long-term experience of Glycine utilization has demonstrated that the optimum efficacy is achieved by a tablet with the decomposition period varying from 10 to 20 minutes, crushing resistance ranging from 10 to 30 N, containing 0.101 g of microcapsuled glycine and 0.001 g of magnesium stearate.

Dissolution of the medicine with the specified composition and physico-chemical properties is attended by buildup of special structures which provide maximum therapeutic effect. In its turn character and degree of structuring by using particular methods render it possible to carry out quantitative assessment of tablet qualitative composition in aqueous medium. (EA B1 No. 7615, IPC 8 GO1N 21/17, 2006). In the process of manufacturing of the medicine Glycine, taking into consideration formulation and low content of adjuncts most difficulties occur with adherence to the interval of decomposition period since amino-acetic acid is easily water-soluble. It is easy to overcome these difficulties if pelletizing mass formulation is adhered to. Glycine plays part of a special ingredient structure in the form of microcapsules (non-agglomerated crystals of amino-acetic acid, filmed by water-soluble methyl-cellulose MC-100) in this formulation whereas a tablet itself as a 'substance' is composition structure, obtained by compression which save to the utmost microcapsules integrity.

Controllable decomposition period can be attained by use of microcapsuled glycine and strict adherence to the particular pelletizing mass formulation. (RU C1 No. 22171673, IPC 7 A61K 9/50, 2001). Preparation of the medicine "Glycine tablets for sublingual applying 0.1 g" of high efficiency requires strict adherence to qualitative and quantitative formulation, use of the particular ingredient structure (microcapsuled Glycine), included in palletizing mass and particular structure of final substance—medicine, that can be achieved upon condition that high production, standards are observed. Taking into account some difficulties in production of the drug "Glycine tablets for sublingual applying 0.1 g" (as related to decomposition period), lack of simple and accessible methods of identification of adjunct substances in the State quality standard of drugs leads to massive violations of the medicine formulation concerning adjunct substances by unscrupulous manufacturers for the purpose of frivolous cheapening. Such violations mostly result in self-tapering action and in some cases loss of its pharmacological effects. In this context it is worthy of note that 140 years after amino-acetic acid had been invented pharmacological effects were obtained only with the particular medicine structure and method of its utilization.

There is known mix for identity test of the medicine- "Glycine tablets for sublingual applying 0.1 g", involving purified water and porphyrized tablets in a ratio 100:1 with light transmission coefficient of 4 ml mix and layer thickness of 10 mm and wave length 700±2 nm in comparison with purified water ranging from 50% to 70%. (pharmacopeia FC 42-0159-05; EA B1 No. 7615, 1PC 8 G01N 21/17, 2006).

It has been shown practically" that the base mix specified makes us evaluate violations of the formulation identity for water-soluble and non-soluble substances. Adjuncts abundance and manufacturers sophistication referring to formulation violation require extra methods of evaluation for adulteration detecting.

SUMMARY OF THE INVENTION

The present complex of inventions is aimed at elaboration of mix and methods of identity test in the process of quality control of the medicine "Glycine tablets for sublingual applying 0.1 g", a metabolic, with stressprotective, antistress, nootropic and neuroprotective effect for single or longterm administration, containing glycine 0.101 g in the form of microcapsules (non-agglomerated crystals filmed by water-soluble methylcellulose, MC-100 or in the form of granulates and magnesium stearate (0.001 g) with decomposition period varying from 10 to 30 minutes and crush resistance from 10 to 30 N. There is set the task of composition identity evaluation which is usually achieved by qualitative and quantitative determination of each component, i.e. the task of quantitative examination (evaluation) of tablet qualitative composition, taking into account the interaction character of medicinal substance and adjunct components in hydro-alcohol medium (50% ethanol) and furthermore in comparison to indicators of quantitative evaluation of tablet qualitative composition and the way of interaction of the medicine and adjunct substances in aqueous medium inclusively.

New quality control means must complete the known quality control methods of "Glycine tablets for sublingual applying 0.1 g" already applied which together with new means must demonstrate that they meet medicine quality requirements providing its optimum therapeutic efficacy.

The given tasks are being accomplished in the following way: there is prepared mix for identity check of the medicine "Glycine tablets for sublingual applying 0.1 g" involving 50% ethanol and porphyrized tablets "Glycine tablets for sublingual applying 0.1 g" in the ratio 100:0.5. Mix preparation method comprises dissolving of 1.25 g of porphyrized tablets in 250 ml of 50% ethanol for 20 minutes at 40° C. in an apparatus for dissolving determination at a paddle rotation speed of 200 rpm. Then mix is allowed for 10 minutes RT (room temperature).

Identification test in the process of quality control of the medicine "Glycine tablets for sublingual applying 0.1 g" involves hydro-alcohol mix preparation using of 50% ethanol as described afore. Then 4 ml of the mix are selected and measured on spectrophotometer for light transmission at a wave length 700±2 nm in a cuvet with layer thickness of 10 mm relative to 50% ethanol. Water mix is prepared by dissolving of 2.5 g of porphyrized tablets in 250 ml of purified water for 20 minutes at 37° C. in the apparatus for dissolving determination at a paddle rotation speed of 150 rpm. Then mix is allowed for 10 minutes, 4 ml of mix selected are subjected to spectrophotometer examination in a cuvet with layer thickness of 10 mm versus purified water at a wave length of 700±2 nm. Later on there is determined difference between light transmission coefficients of hydro-alcohol mix and water mix and the result obtained is compared to the limit of 30% to 50%.

The mix and techniques described aid to test efficiently identity of the medicine "Glycine tablets for sublingual applying 0.1 g" since adjuncts not specified by the actual formulation, are water- or alcohol-soluble that is different from the solubility of the actual components. Adjuncts added by unscrupulous manufacturers for the purpose to get the required decomposition period are easy water-soluble and endowed with bounding effect, increase light transmission value up to 70-90% (instead of 50-70%). Addition of non-water-soluble adjuncts (e.g. talc, chalk etc) with different alcohol-solubility degree is defined due to mix investigation on base of 50% ethanol with further estimation of difference in light transmission values of hydro- alcohol and water mixes.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

DETAILED DESCRIPTION OF THE PREFERRED EMBODIMENTS

Quality control of the medicine "Glycine tablets for sublingual applying 0.1 g." for each batch is carried out in laboratories of quality control departments in pharmaceutical companies and in test-laboratories of certification centers.

Hydro-alcohol and water mixes are prepared simultaneously and consistently. Hydro-alcohol mix is prepared by dissolving of 1.25 g (precision weight) of porphyrized tablets in 250 ml of 50% ethanol for 20 minutes at a temperature of 40° C. in the apparatus for dissolving determination, paddle "Erweka" at a paddle rotation speed of 200 rpm. Then mix is allowed for 10 minutes RT and 4 ml of the mix selected are subjected to spectrophotometer examination at a wave length of 700±2 nm in a cuvet with layer thickness of 10 mm versus 50% ethanol.

Water mix is prepared by dissolving of 2.5 g of porphyrized tablets in 250 ml of purified water for 20 minutes at 37° C. in the apparatus for dissolving determination, paddle "Erweka" at a paddle rotation speed of 150 rpm. Then mix is allowed for 10 minutes RT, 4 ml of mix selected are subjected to spectrophotometer examination in a cuvet with layer thickness of 10 mm versus purified water at a wave length of 700±2 nm. Light transmission coefficient of hydro-alcohol mix must lie within the limits (90-100%). Light transmission coefficient of water mix must vary from 50% to 70%.

There is determined difference between light transmission coefficients of hydro-alcohol and water mixes. The value obtained ranging from 30% to 50% corresponds to appropriate composition and quality of the medicine "Glycine tablets for sublingual applying 0.1 g." endowed with the necessary therapeutic effect.

Confirmation of interaction of the "Glycine tablets for sublingual applying 0.1 g" determinate quantity and quality content and light transmission values is demonstrated in the table presenting the analysis results made in accordance with the below examples.

EXAMPLE 1

1.25 g. of the porphyrized "Glycine tablets for sublingual applying 0.1 g." were dissolved in 250 ml of 50% ethanol for 20 minutes at 40° C. in the apparatus for dissolving determination, paddle "Erweka" at a paddle rotation speed of 200 rpm. Decomposition period of tablets with mottle elements varied from 10 to 20 minutes, resistance ranged from 10 to 30N. The tablets contained 0.101 g. of microcapsulated glycine and 0.001 g of magnesium stearate.

On complete dissolution of the tablets obtained after porphyrizing within 20 minutes, mix was allowed for 10 minutes RT, then there were selected 4 ml of mix in a cuvet with layer thickness of 10 mm and later subjected to spectrophotometer examination versus solvent (50% ethanol) at a wave length of 700±2 nm.

Light transmission coefficient was 98.6%.

2.5 g of the porphyrized "Glycine tablets for sublingual applying 0.1 g." (formulation and physico-chemical properties were mentioned before) were dissolved in 250 ml of water for 20 minutes at 37° C. in the apparatus for dissolving determination, paddle "Erweka" at a paddle rotation speed of 150 rpm.

On complete dissolution of powder within 20 minutes, mix was allowed for 10 minutes RT, then there were selected 4 ml of mix in a cuvet with layer thickness of 10 mm and later subjected to spectrophotometer examination versus solvent (purified water) at a wave length of 700±2 nm. Light transmission coefficient was 63%.

Difference in light transmission coefficients of hydro-alcohol and water mixes is 35.6%.

In the similar way there were prepared mixes with tablets containing amino-acetic acid 0.1 g, water-soluble methylcellulose, MC-100-0.001 g in granulates and magnesium stearate 0.001 g. in the function of powder.

The results are presented in the table below.

EXAMPLE 2

1.25 g. of the porphyrized tablets containing 0.1 g of amino-acetic acid, 0.001 g of water-soluble methylcellulose, MC-100 and 0.001 g calcium stearate, were dissolved in 250 ml of 50% ethanol according the run of example 1.

Light transmission coefficient was 63%.

2.5 g of the porphyrized tablets containing 0.1 g of amino-acetic acid, 0.001 g of water-soluble methylcellulose, MC-100 and 0.001 g of calcium stearate, were dissolved in 250 ml of water according the run of example 1.

Light transmission coefficient was 62%.

Difference in light transmission coefficients of hydro-alcohol and water mixes is 1%.

EXAMPLE 3

1.25 g. of the porphyrized tablets containing 0.1 g of amino-acetic acid, 0.001 g of water-soluble methylcellulose, MC-100, 0.0005 g of magnesium stearate and 0.0005 g of calcium stearate, were dissolved in 250 ml of 50% ethanol according the run of examples 1 and 2. Light transmission coefficient was 70%.

2.5 g of the porphyrized tablets containing 0.1 g of amino-acetic acid, 0.001 g of water-soluble methylcellulose, MC-100, 0.0005 g of magnesium stearate and 0.0005 g of calcium stearate, were dissolved in 250 ml of water according the run of examples 1 and 2.

Light transmission coefficient was 62%.

Difference in light transmission coefficients of hydro-alcohol and water mixes was 8%.

EXAMPLE 4

In order to obtain hydro-alcohol and water mixes there were used tablets containing 0.1 g of amino-acetic acid, 0.0005 g of water-soluble methylcellulose, MC-100, and 0.0005 g of magnesium stearate.

All investigations were carried our in a way similar to examples 1 and 2. Light transmission coefficient of hydro-alcohol mix was 99%. Light transmission coefficient of water mix was 79%. Difference amounted to 20%.

EXAMPLE 5

In order to obtain hydro-alcohol and water mixes there were used tablets (the medicine Glicised-KMP batches 14.08.05, 15.09.05), involving 0.1 g of amino-acetic acid and adjunct components in unknown quantities: oydragit RS-30D, montaniae glycolic wax, polyvinylpirrolidone low-molecular medicinal and calcium stearate.

Experiments were held according to the run of examples 1 and 2.

Light transmission coefficient of hydro-alcohol mix corresponded to 74.7% and 72.7%.

Light transmission coefficient of water mix corresponded to 55% and 59%. Difference amounted to 19.7%, 13.2%.

EXAMPLE 6

In order to obtain hydro-alcohol and water mixes there were used tablets (Gromecine batches 05.07.06, 07.07.06), involving 0.1 g of amino-acetic acid, 0.001 g of water-soluble methylcellulose, MC-100, and 0.001 g of magnesium stearate, in accordance with the instruction. Experiments were held according to the run of examples 1 and 2.

Light transmission coefficient of hydro-alcohol mix was 97.1%, 98.3%. Light transmission coefficient of water mix was 76.9%, 90.1%. Difference-20.2%, 8.2%.

TABLE

| Example No | Quantitative and qualitative content | Light transmission coefficient in 50% ethanol (1), % | Light transmission coefficient of water (2), % | Difference in light transmission coefficients (1-2), % |
|---|---|---|---|---|
| 1 | amino-acetic acid 0.1 g, water-soluble methylcellulose, MC-100—0.001 g, magnesium stearate 0.001 g | 98.6<br>99.7 | 63.0<br>60.2 | 35.6<br>39.5 |
| 2 | amino-acetic acid 0.1 g, water-soluble methylcellulose, MC-100—0.001 g, calcium stearate 0.001 g | 63 | 62 | 1 |
| 3 | amino-acetic acid 0.1 g, water-soluble methylcellulose, MC-100—0.001 g, magnesium stearate 0.0005 g, calcium stearate 0.0005 g | 70.6 | 62.5 | 8.1 |
| 4 | amino-acetic acid 0.1 g, water-soluble methylcellulose, MC-100—0.0005 g, lactose 0.001 g magnesium stearate 0.0005 g | 99.2 | 79 | 20.2 |
| 5 | amino-acetic acid 0.1 g oydragit RS-30D, montaniac glycolic wax, polyvinylpirrolidone lowmolecular medicinal calcium stearate | 74.7<br>72.7 | 55<br>59.5 | 19.7<br>13.2 |
| 6 | amino-acetic acid 0.1 g, water-soluble methylcellulose, MC-100, magnesium stearate | 97.1<br>98.3 | 76.9<br>90.1 | 20.2<br>8.2 |
| 7 | amino-acetic acid 0.1 g, water-soluble methylcellulose, MC-100—0.001 g, magnesium stearate—0.001 g | 77.9 | 38.0 | 39.9 |

EXAMPLE 7

In order to obtain hydro-alcohol and water mixes there were used tablets (produced by company OOO "Vicher-Pharm"), involving 0.1 g of amino-acetic acid, 0.001 g of water-soluble methylcellulose. MC-100, and 0.001 g of magnesium stearate, batch 03.03.04 in accordance with the instruction. Experiments were held according to the run of examples 1 and 2.

Light transmission coefficient of hydro-alcohol mix was 77.9%.

Light transmission coefficient of water mix was 38.0%. Difference-39.9%.

While this invention has been particularly shown and described with references to preferred embodiments thereof, it will be understood by those skilled in the art that various changes in form and details may be made therein without departing from the scope of the invention encompassed by the appended claims.

What is claimed is:

1. A mixture for quality control of 0.1 g glycine tablets for sublingual application, the tablets having stress-preventative, anti-stress, nootropic and neuroprotective effects, the tablets being suitable for single administration or for long-term treatment, each tablet comprising microcapsulated glycine comprising non-agglomerated crystals of amino-acetic acid covered with a polymeric film of water-soluble methycellulose, each tablet further comprising magnesium stearate and each tablet having a crush resistance ranging from 10 to 30 N and a decomposition period varying from 10 to 20 minutes, the mixture comprising:

50% ethanol and the 0.1 g glycine tablets that have been porphyrized in a ratio of 100:0.5, wherein a sample of 4 ml of the mixture with a layer thickness of 10 mm has a light transmission coefficient at a wavelength of 700±2 nm in comparison with 50% ethanol within the limits of 90% to 100%.

2. A method of preparing a mixture for quality control of 0.1 g glycine tablets for sublingual application, the tablets having stress-preventative, anti-stress, nootropic and neuroprotective effects, the tablets being suitable for single administration or for long-term treatment, each tablet comprising microcapsulated glycine comprising non-agglomerated crystals of amino-acetic acid covered with a polymeric film of water-soluble methycellulose, each tablet further comprising magnesium stearate and each tablet having a crush resistance ranging from 10 to 30 N and a decomposition period varying from 10 to 20 minutes, the method comprising:

providing said tablets that have been porphyrized;

obtaining the mixture by mixing 1.25 g of porphyrized tablets in 250 ml of 50% ethanol for 20 minutes at a temperature of 40° C. in an apparatus using a paddle rotation speed of 200 revolutions per minute;

allowing the mixture to stand for 10 minutes at room temperature;

and measuring a light transmission coefficient of 4 ml of the mixture for a 10 mm thick layer in a container relative to the light transmission coefficient for 50% ethanol using a light transmission spectrophotometer at a wavelength of 700±2 nm.

3. A method for performing an identification test for quality control of 0.1 g glycine tablets for sublingual application, the tablets having stress-preventative, anti-stress, nootropic and neuroprotective effects, the tablets being suitable for single administration or for long-term treatment, each tablet comprising microcapsulated glycine comprising non-agglomerated crystals of amino-acetic acid covered with a polymeric film of water-soluble methycellulose, each tablet further comprising magnesium stearate and each tablet having a crush resistance ranging from 10 to 30 N and a decomposition period varying from 10 to 20 minutes, the method comprising:

preparing a hydro-alcohol mixture by dissolving 1.25 g of the 0.1 g glycine tablets which have been porphyrized in 250 ml of 50% ethanol for 20 minutes at a temperature of 40° C. in an apparatus using a paddle rotation speed of 200 revolutions per minute; allowing the mixture to stand for 10 minutes at room temperature; and measuring a light transmission coefficient of 4 ml of the hydro-alcohol mixture for a 10 mm thick layer in a container relative to the light transmission coefficient for 50% ethanol using a light transmission spectrophotometer at a wavelength of 700±2 mm;

preparing a water mixture by dissolving 2.5 g of the 0.1 g glycine tablets which have been porphyrized in 250 ml of purified water for 20 minutes at a temperature of 37° C. in an apparatus using a paddle rotation speed of 150 revolutions per minute; allowing the mixture to stand for 10 minutes at room temperature; and measuring a light transmission coefficient of 4 ml of the water mixture for a 10 mm thick layer in a container relative to the light transmission coefficient for purified water using a light transmission spectrophotometer at a wavelength of 700±2 nm;

determining the difference between the light transmission coefficients of the hydroalcohol mixture and the water mixture; and comparing the difference with a limit of 30 to 50%.

* * * * *